United States Patent
Kim et al.

(10) Patent No.: US 6,222,903 B1
(45) Date of Patent: Apr. 24, 2001

(54) LAMINOGRAPHY SYSTEM HAVING A VIEW SELECTOR WITH PRISM

(75) Inventors: Hyeong-cheol Kim, Sungnam; Jong-eun Byun; Jin-young Kim, both of Seoul; Chang-hyo Kim, Sungnam; Hyung Seok Cho, Daejeon; Kuk-won Ko, Daejeon; Young-jun Roh, Daejeon, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/261,494

(22) Filed: Mar. 3, 1999

(30) Foreign Application Priority Data

Sep. 30, 1998 (KR) .................................................. 98-40955

(51) Int. Cl.[7] ...................................................... A61B 6/00
(52) U.S. Cl. ................................................ 378/22; 378/39
(58) Field of Search ................................... 378/22, 39, 4, 378/10, 19, 20, 21

(56) References Cited

U.S. PATENT DOCUMENTS

| | | | |
|---|---|---|---|
| 4,926,452 | 5/1990 | Baker et al. | 378/22 |
| 5,259,013 | * 11/1993 | Kuriyama et al. | 378/43 |
| 5,533,087 | * 7/1996 | Snoeren | 378/98.3 |
| 5,594,770 | 1/1997 | Bowles et al. | 378/58 |
| 6,038,286 | * 3/2000 | Wagli et al. | 378/22 |

FOREIGN PATENT DOCUMENTS 5-312735    11/1993    (JP) .

* cited by examiner

Primary Examiner—Robert H. Kim
Assistant Examiner—Irakli Kiknadze
(74) Attorney, Agent, or Firm—Burns, Doane, Swecker & Mathis, L.L.P.

(57) ABSTRACT

A laminography system includes a table, an X-ray source, an image intensifier, a view selector and a camera. The view selector has a prism for refracting a ray of light, and an adjusting part for adjusting the prism to a position in which images at a certain area of an image projecting plane of the image intensifier are received into the camera. The adjusting part has a first motor for rotating the prism along the circumferential direction of the image intensifier, and a second motor for rotating the prism in a direction perpendicular with respect to a radial direction of the image intensifier. Accordingly, the images at any areas of the image projecting plane of the image intensifier can be obtained. In addition, since an optical axis of the image passing through the prism and then received into the camera is in perpendicular relation with the camera, no image distortions occur.

3 Claims, 10 Drawing Sheets

LAMINOGRAPHY SYSTEM HAVING A VIEW SELECTOR WITH PRISM

BACKGROUND OF THE INVENTION

1. Field of the Invention

The present invention relates to a laminography system for obtaining an image of lamina of a test object, thereby inspecting interior of the test object, which are not observed with the naked eye.

2. Description of the Prior Art

Generally, various quality inspections are carried out during the manufacturing of industrial products in order to confirm whether the products are acceptable or not. Among these, a laminography system is utilized for the inspection of certain areas hardly observed with the naked eye, such as solder connections of electronic devices mounted on a printed circuit board, or the like.

Construction and operation of a prior art laminography system is described hereinbelow.

As shown in FIG. 1, a laminography system 1 includes a table 10, an X-ray source 20, an image intensifier 30, a view selector 40, and a camera 50. X-rays irradiated from the X-ray source 20 rotate along the circumference of the X-ray source 20 with a predetermined speed. Such rotating X-rays are transmitted through a test object E which is loaded on the table 10. The X-rays transmitted through the test object E produce images on an image projecting plane 32.

At this time, due to the different positions from which the rotating X-rays are irradiated, the images are projected onto different portions of the image projecting plane 32 as shown in FIG. 2. The images on the respective portions of the image projecting plane 32 are then interposed on one another, and an image of a lamina is obtained.

Generally, due to the rotation of the X-rays along the circumference of the X-ray source 20, the image transmitted through the test object E rotates on the image projecting plane in the circumferential direction thereof. Therefore, the images are selected in order by the view selector 40, and received into the camera 50.

The above-described view selector 40 guides the images from the respective areas of the image projecting plane 32 into the camera 50 by means of a pair of mirrors. U.S. Pat. Nos. 4,926,452 and 5,594,770 disclose typical examples of such view selector.

According to the view selector of U.S. Pat. No. 4,926,452 as shown in FIG. 3, a pair of mirrors 42' and 44' facing each other are rotated together with the images rotating along the circumference of the image projecting plane 32, so that the mirrors 42' and 44' guide the images into the camera 50. Here, the mirrors 42' and 44' and images are rotated together at the same speed. Meanwhile, FIG. 4 shows the view selector of U.S. Pat. No. 5,594,770 in which a pair of mirrors 42" and 44" are disposed under the image intensifier in such a manner that the mirrors 42" and 44" can be rotated respectively about an X-axis and an Y-axis. Thus, when the images are moved on the image projecting plane 32 disposed on the image intensifier, the mirrors 42" and 44" are rotated about the X, and Y-axes so as to select the image of a certain area. Accordingly, as the images on the image projecting plane 32 are reflected on the mirrors 42" and 44" in subsequent order, the images are sequentially received into the camera 50. The reference numerals 43" and 45" in FIG. 4 denote motors for rotating the mirrors 42" and 44".

According to the view selector of U.S. Pat. No. 4,926,452, however, the view selector is operated only when the images are moving in the circumferential direction of the image projecting plane. Further, the view selector of that patent has a drawback in that the images at the center portion of the image intensifier can not be easily obtained. The view selector of U.S. Pat. No. 5,594,770 has the possibility of having image distortions due to the fact that the angle of incidence of the X-rays keeps changing in accordance with the different positions of the images.

SUMMARY OF THE INVENTION

An object of the present invention is to provide a laminography system capable of obtaining every image projected on every portion of an image projecting plane without image distortions.

Above-mentioned object is accomplished by a laminography system of the present invention including a table, an X-ray source, an image intensifier, a view selector and a camera. The view selector has a prism for refracting a ray of light, and an adjusting section for adjusting the prism to a position in which image of certain area of an image projecting plane of the image intensifier can be received into the camera.

The adjusting part has a first motor for rotating the prism along the circumferential direction of the image intensifier, and a second motor for rotating the prism in a direction perpendicular with respect to a radial direction of the image intensifier. Additionally, a mirror can be disposed at the position corresponding to the central portion of the image intensifier of the prism so as to refract the image at the central portion of the image intensifier into another camera.

Alternatively, a pair of prisms can be disposed at a lower side of the image intensifier in such a manner that the prisms rotate respectively about an X-axis and an Y-axis. As the adjustment parts, a pair of motors rotate the prisms about X-axis and Y-axis.

BRIEF DESCRIPTION OF THE DRAWINGS

The above object and advantages will be more apparent by describing preferred embodiments in greater detail with reference to the drawings accompanied, in which.

DETAILED DESCRIPTION OF THE PREFERRED EMBODIMENTS

Figure 1:
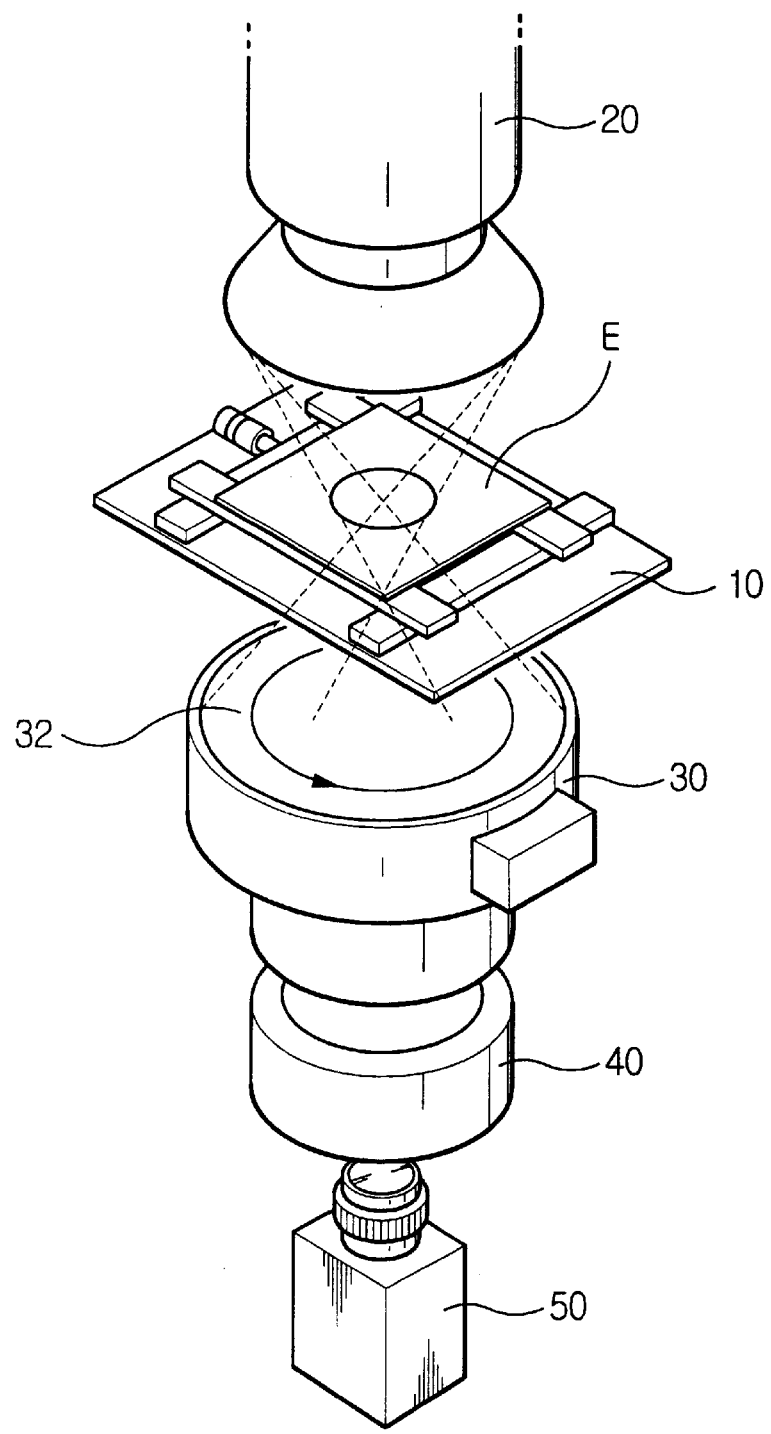
FIG. 1 is a perspective view showing a construction of a conventional laminography system.
Figure 2:
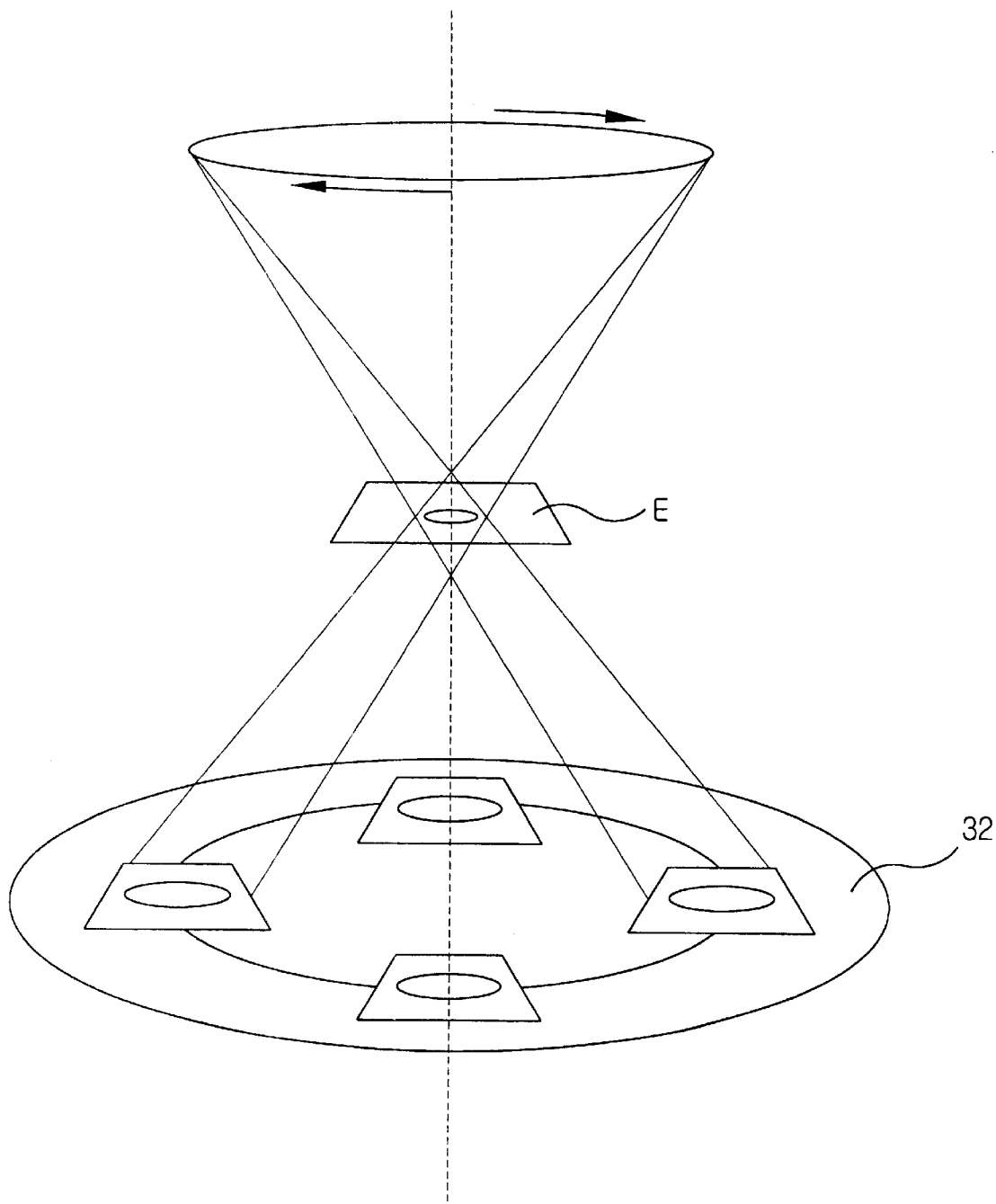
FIG. 2 is a view showing the conventional laminography system having lamina images varying in positions in accordance with the positions X-rays are irradiated.
Figure 3:
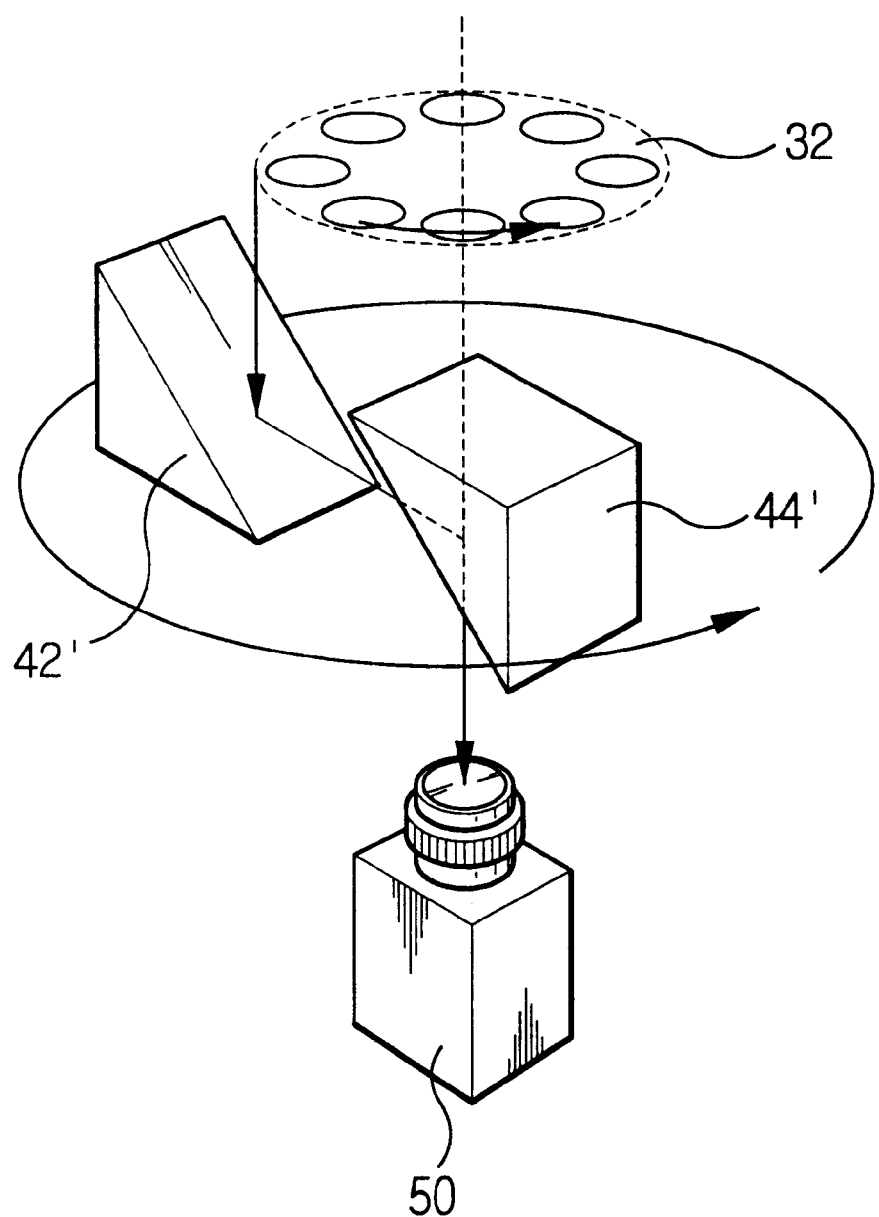
FIG. 3 is a schematic representation showing one example of a view selector employed into a conventional laminography system.
Figure 4:
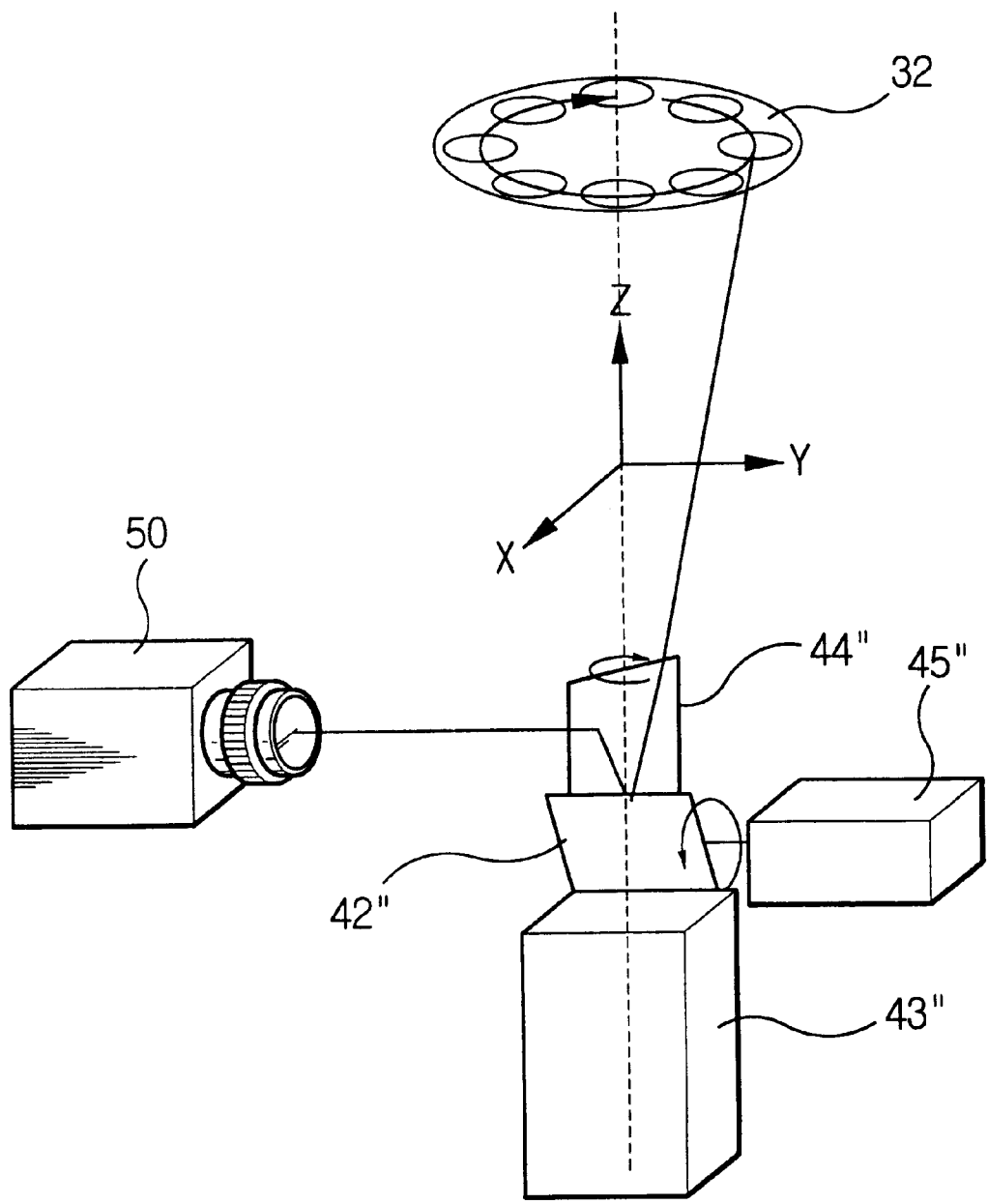
FIG. 4 is a schematic representation showing another example of the view selector employed into the conventional laminography system.

A laminography system of the present invention basically has a similar construction with that of the related art shown in FIG. 1. That is, the laminography system of the present invention has a table 10 onto which a test object E is loaded, an X-ray source 20 for irradiating X-rays over the test object E loaded on the table 10, an image intensifier 30 for converting the X-rays transmitted through the test object E into visible images, a view selector 40 for selecting certain area of an image projecting plane 32, and a camera 50 for obtaining the image selected by the view selector. The X-rays irradiated from the X-ray source 20 are transmitted through the test object E loaded on the table 10 and converted into the visible images before they are projected on the image projecting plane 32. Then, the view selector selects a certain area of the image projecting plane 32 of the image intensifier 30. Accordingly, the images at the selected area are received into the camera 50. (Hereinbelow, the like elements will be given the same reference numerals).

The unique aspect of the present invention relates to the view selector. That is, unlike the view selector 40 of the related art which employs a mirror to reflect a ray of light, the view selector 40' of the present invention has a prism 110 which refracts the ray of light to select the certain area of the image projecting plane 32.

Figure 5:
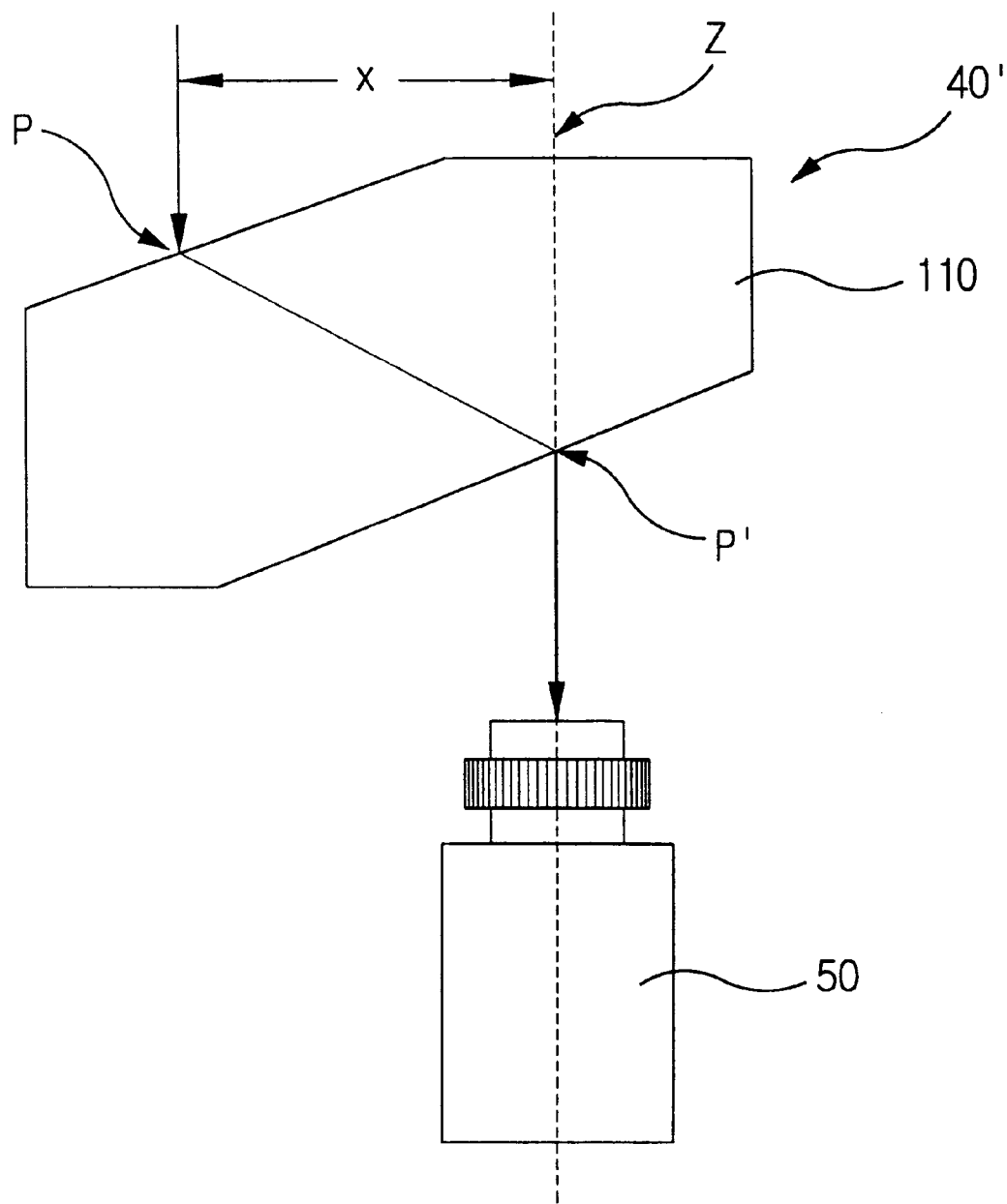
FIG. 5 is a schematic view for explaining a principle of a prism employed into a view selector of the present invention.

As is generally known, the prism 110 refracts a ray of light so that it varies the path of the light. Thus, as shown in FIG. 5, the incident ray on the prism 110 is refracted to a position P' distanced from the incident point P of the initial ray by a width X as it passes through the prism 110, so that the ray of light is received into the camera 50. By utilizing such an aspect of a prism, i.e., by disposing the prism 110 beneath the image intensifier and adjusting the position of the prism 110, the images of every area of the image projecting plane on the image intensifier can be received into the camera 50.

The first preferred embodiment of the present invention will be described hereinbelow.

Figure 6:
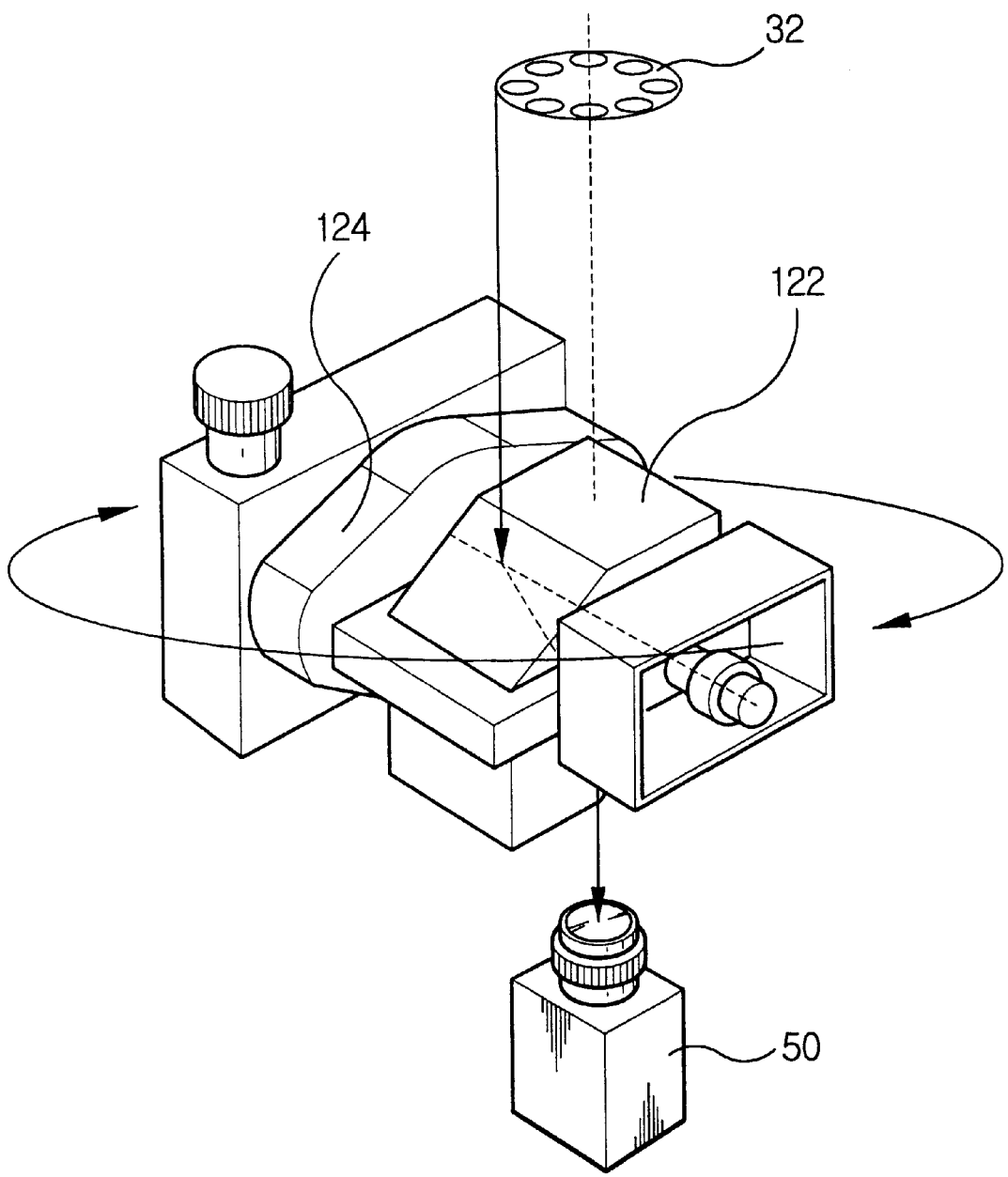
FIG. 6 is a schematic perspective view showing a view selector according to a first preferred embodiment of the present invention.

As shown in FIG. 6, the view selector 40' of the laminography system according to the first preferred embodiment of the present invention has a prism 122 of a predetermined degree of refractive index, a first motor (not shown) for rotating the prism 122 in the circumferential direction of the image projecting plane 32 on the image intensifier, i.e., about an axis Z, and a second motor 124 for rotating the prism 1 22 about an axis L extending perpendicular to the axis Z, i.e., in a perpendicular direction with respect to the radial direction of the image projecting plane 32.

Figure 7A:
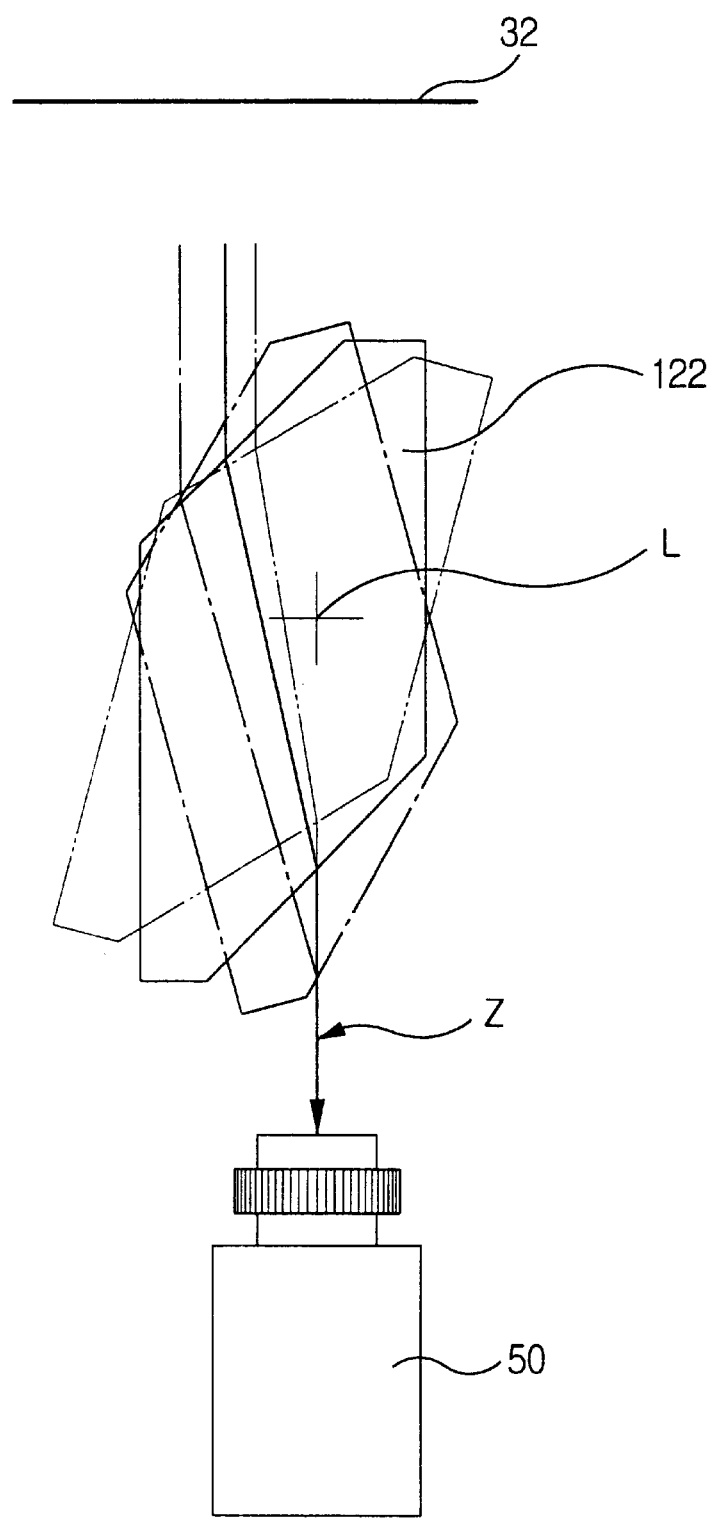
FIG. 7A is a schematic view showing an operation of a view selector according to the first preferred embodiment of the present invention.

Thus, the first motor rotates the prism 122 about an axis Z (FIG. 5) so that the prism 122 is rotated in the circumferential direction with the same speed as that of the images projected on the image projecting plane 32 of the image intensifier. Consequentially, the images projected on the image projecting plane 32 and rotating in a circle having a radius corresponding to the horizontal distance that the X-ray is refracted are sequentially received into the camera 50. In addition, as shown in FIG. 7A, by adjusting the angle by which the prism 122 is slanted, via the motor 124, the distance X that the X-ray is refracted can be varied. Thus, it is possible to easily obtain all the images rotating in each circle of radius of rotation. Due to the presence of the prism 122, the optical axis of the image received into the camera 50 is in perpendicular relation with the camera 50, so that the image distortions are prevented.

Figure 7B:
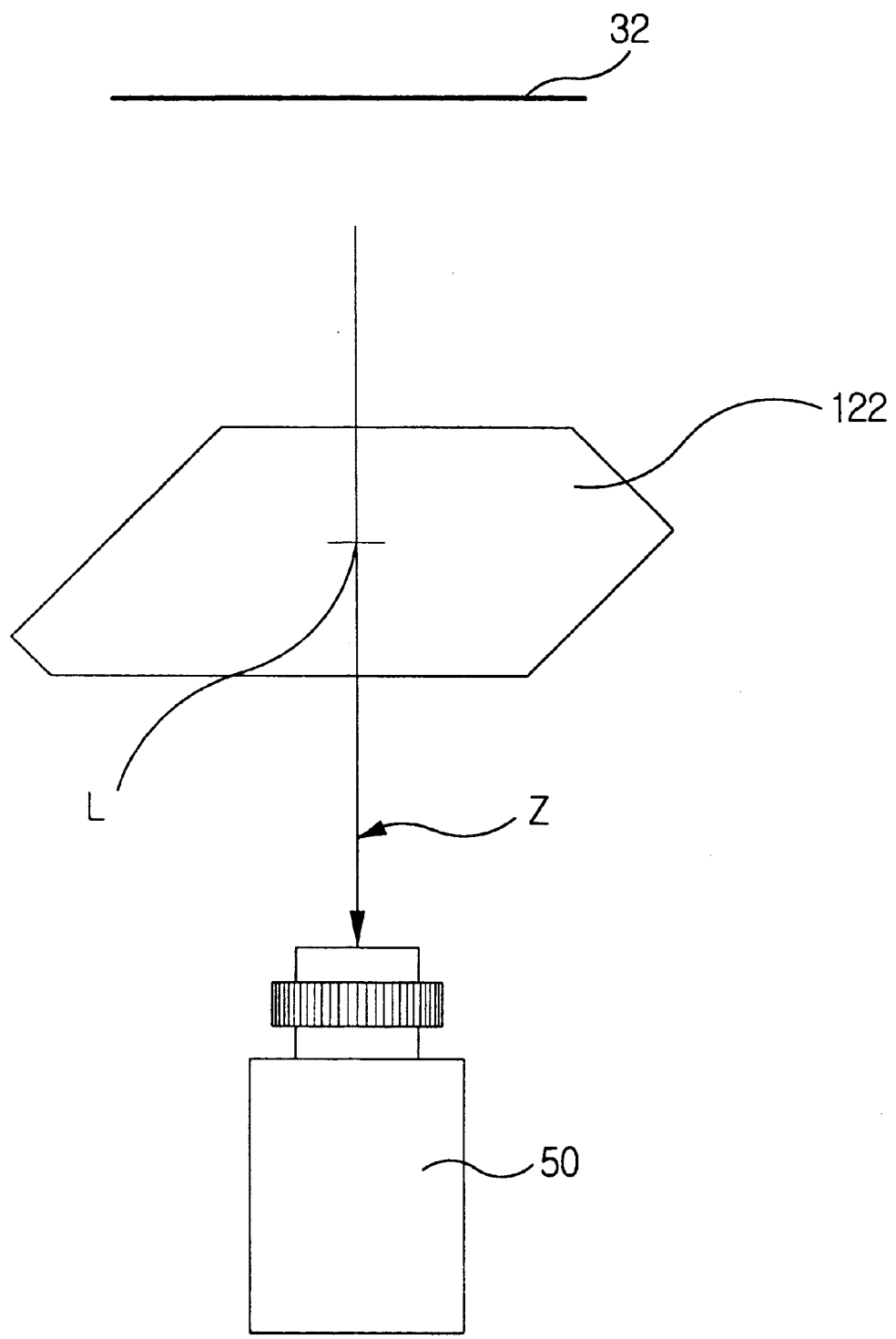
FIG. 7B is a schematic view showing a way that a view selector according to the first preferred embodiment of the present invention obtains an image at a central portion of an image projecting plane.

In addition, not only can there be obtained the images at the circumference of the image projecting plane, but also the images at the central portion of the image projecting plane can be obtained. That is, by rotating the prism 122 to a horizontal state as shown in FIG. 7B, the distance X that the light is refracted becomes zero. Thus, the ray of light is not refracted but directly passes through the prism 122, and the undistorted images of the central portion of the image projecting plane 32 are received into the camera 50.

Figure 7C:
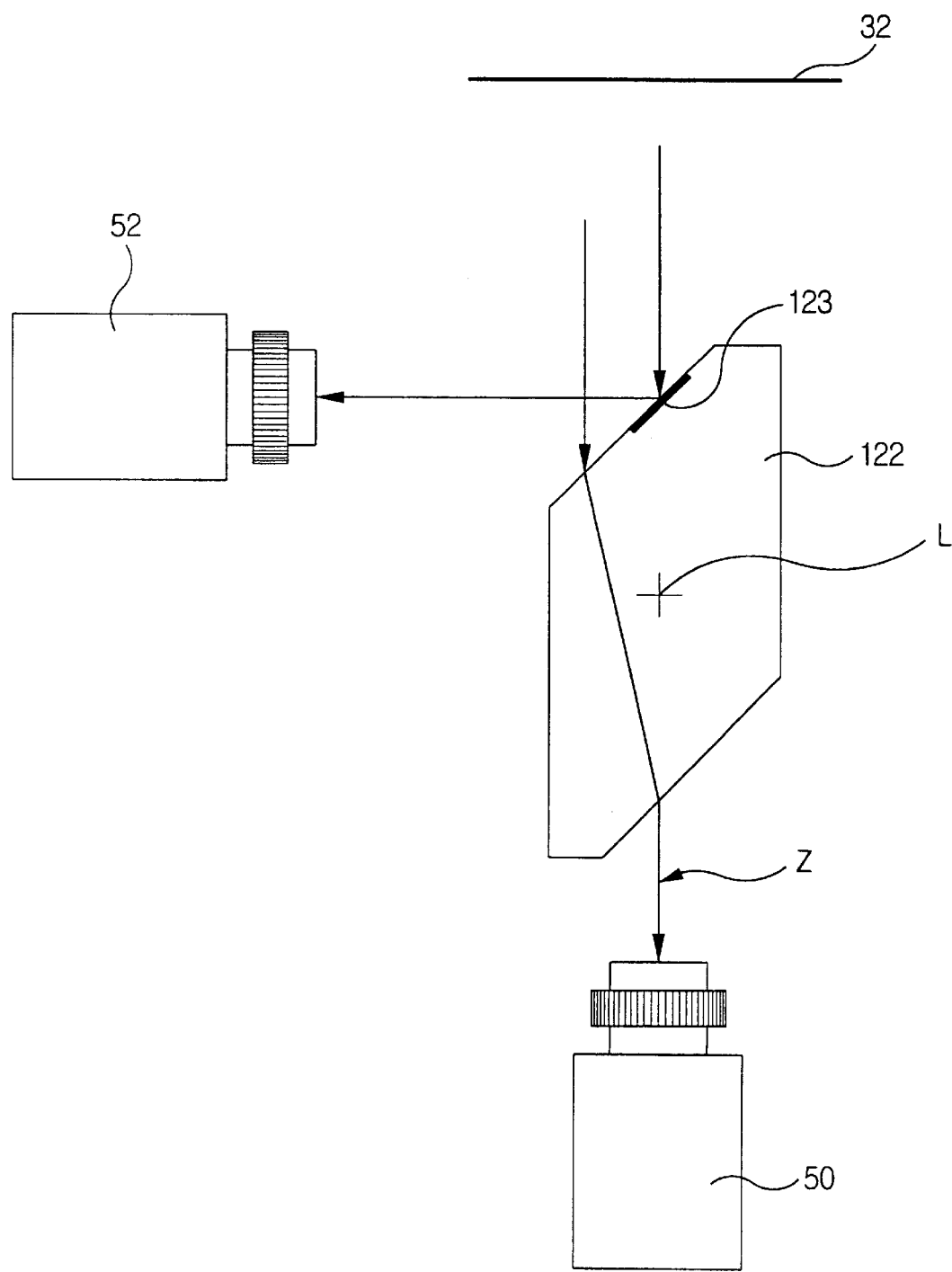
FIG. 7C is a schematic view showing another way that a view selector according to the first preferred embodiment of the present invention obtains an image at the central portion of the image projecting plane.

Forming a mirror part 123 at a side of the prism 122 can be an alternative way of obtaining the images at the central portion of the image projecting plane 32, as shown in FIG. 7C. The mirror part 123 lies on the same axis line with the camera 50. Another camera 52 is disposed at the position to which the light is reflected by the mirror part 123. Thus, the images at the central portion of the image projecting plane 32 are reflected by the mirror part 123, and are received into the another camera 52.

Figure 8:
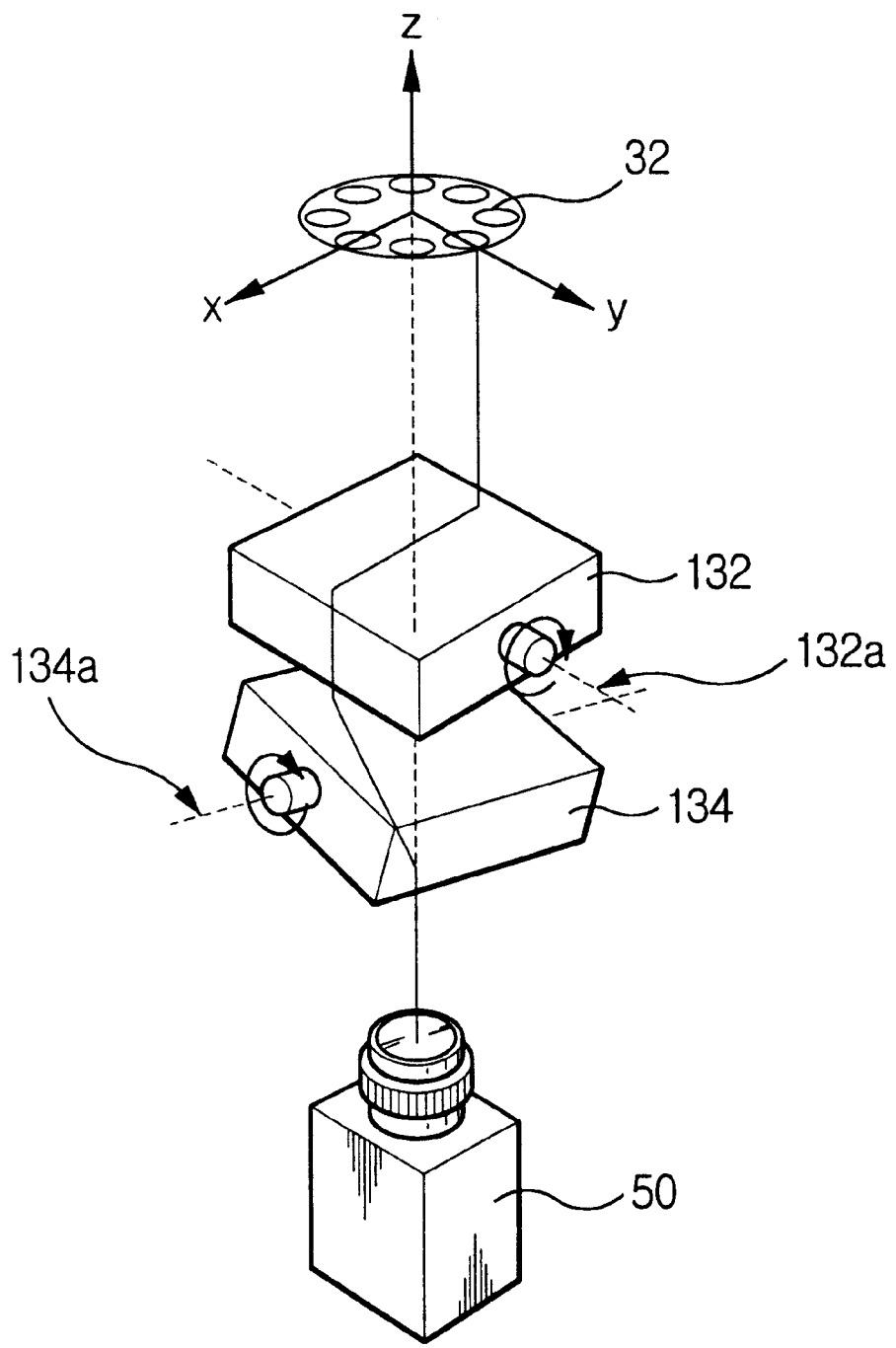
FIG. 8 is a schematic perspective representation showing a view selector according to the second preferred embodiment of the present invention.

Meanwhile, FIG. 8 is a view showing a construction of the view selector according to a second preferred embodiment of the present invention. According to the second preferred embodiment, a pair of prisms 132 and 134 are employed. That is, the prisms 132 and 134 are disposed between the image projecting plane 32 and the camera 50 in parallel relation with each other. The prisms 132 and 134 are rotated respectively about a Y-axis 132a and an X-axis 134a, and degrees of rotation are respectively adjusted by the motors (not shown) respectively connected with rotary shafts of the prisms 132 and 134. The upper prism 132 varies the light path with respect to the X-axis, while the lower prism 134 varies the light path with respect to the Y-axis.

Thus, as the prisms 132 and 134 are rotated in perpendicular relation with each other, the respective degrees that the prisms 132 and 134 are slanted are adjusted, so that the images at any areas of the image projecting plane 32 can be received into the camera 50.

As described above, according to the present invention, the images at all the area of the image projecting plane 32 can be obtained by adjusting the position of the prism. In addition, since the optical axis of the images received into the camera 50 are in perpendicular relation with the camera 50, the image distortions are prevented.

While the present invention has been particularly shown and described with reference to the preferred embodiments thereof, it will be understood by those skilled in the art that various changes in form and details may be effected therein without departing from the spirit and scope of the invention as defined by the appended claims.

What is claimed is:

1. A laminography system comprising:
   a table for supporting a test object;
   an X-ray source for irradiating X-rays onto a test object supported by the table, the X-rays projected from various positions in a common plane;
   an image intensifier for converting X-ray images transmitted through the test object into visible images, the visible images emitted from the image intensifier along a circumferential path having a geometric center, the image intensifier defining an image projecting plane;

a view selector having a prism for receiving and refracting a light from the image intensifier, and an adjustment mechanism connected to the prism for adjusting the prism to a position in which images of a certain area of the image projecting plane can be selected, the adjustment mechanism comprising a first motor for rotating the prism about a first axis coinciding with the geometric center, and a second motor for rotating the prism about a second axis extending substantially perpendicular to the first axis;

a first camera positioned for obtaining the images of the selected area;

a second camera; and a mirror part disposed at a central area of the prism intersected by the first axis, the mirror arranged to reflect images to the second camera.

2. The laminography system as claimed in claim 1 wherein the prism constitutes a first prism, and further including a second prism disposed beneath the first prism; the second prism rotatable about a third axis extending perpendicular to each of the first and second axes.

3. A laminography system comprising:

a table for supporting a test object;

an X-ray source for irradiating X-rays onto a test object supported by the table, the X-rays projected from various positions in a common plane;

an image intensifier for converting X-ray images transmitted through the test object into visible images, the visible images emitted from the image intensifier along a circumferential path having a geometric center, the image intensifier defining an image projecting plane;

a view selector having a first prism for receiving and refracting a light from the image intensifier, and an adjustment mechanism connected to the first prism for adjusting the first prism to a position in which images of a certain area of the image projecting plane can be selected, the adjustment mechanism comprising a first motor for rotating the first prism about a first axis coinciding with the geometric center, and a second motor for rotating the first prism about a second axis extending substantially perpendicular to the first axis;

a camera positioned for obtaining the images of the selected area; and a second prism disposed beneath the first prism, the second prism rotatable about a third axis extending perpendicular to each of the first and second axes.

* * * * *